US010302667B2

(12) United States Patent
Ferihumer et al.

(10) Patent No.: US 10,302,667 B2
(45) Date of Patent: May 28, 2019

(54) LABORATORY SAMPLE CONTAINER CARRIER HANDLING APPARATUS AND LABORATORY SYSTEM

(71) Applicant: Roche Diagnostics Operations, Inc., Indianapolis, IN (US)

(72) Inventors: Harald Ferihumer, Hitzkirch (CH); Christoph Ludwig, Rotkreuz (CH); Beat Jaeggi, Lucerne (CH); Patrik Imfeld, Emmenbruecke (CH)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 226 days.

(21) Appl. No.: 15/404,593

(22) Filed: Jan. 12, 2017

(65) Prior Publication Data
US 2017/0212140 A1 Jul. 27, 2017

(30) Foreign Application Priority Data
Jan. 22, 2016 (EP) ..................... 16152363

(51) Int. Cl.
*G01N 35/04* (2006.01)
*G01N 1/28* (2006.01)
*G01N 1/00* (2006.01)

(52) U.S. Cl.
CPC ............ *G01N 35/04* (2013.01); *G01N 1/28* (2013.01); *G01N 2001/002* (2013.01); *G01N 2035/0439* (2013.01); *G01N 2035/0465* (2013.01)

(58) Field of Classification Search
CPC ..... G01N 35/04; G01N 1/28; G01N 2001/002
(Continued)

(56) References Cited

U.S. PATENT DOCUMENTS 1,892,206 A 12/1932 Dietz
2,417,823 A 3/1947 Hodson et al.
(Continued)

FOREIGN PATENT DOCUMENTS

CN 2646101 Y 10/2004
CN 201133910 Y 10/2008
(Continued)

OTHER PUBLICATIONS

Extended European Search Report dated Jul. 15, 2016 in Application No. 16152363.4, 9 pages.

*Primary Examiner* — Robert R Raevis
(74) *Attorney, Agent, or Firm* — Roche Diagnostics Operations, Inc.

(57) ABSTRACT

A sample container carrier handling apparatus is presented. A first revolving device located at a first level moves sample container carriers along a first path. A second revolving device located at a second level different from the first level moves sample container carriers along a second path. A first transport device transports sample container carriers to or away from a first handover position associated with the first revolving device. A second transport device transports sample container carriers to or away from a second handover position associated with the second revolving device. A lifting device lifts a sample container carrier from a first lifting position associated with the first revolving device to a second lifting position associated with the second revolving device. An operating position is associated with the first or second revolving device. A sample container is loaded or unloaded into a sample container carrier placed at the operating position.

14 Claims, 2 Drawing Sheets

(58) Field of Classification Search
USPC .......... 422/63–65, 67; 414/222.01, 222.07, 414/222.09, 222.11, 223.01, 223.02, 414/798.2, 798.9, 788; 436/43, 47, 48, 436/49; 73/863, 863.01, 864.21, 864.23
See application file for complete search history.

(56) References Cited

U.S. PATENT DOCUMENTS

| | | | |
|---|---|---|---|
| 2,628,708 A | 2/1953 | Wahl et al. |
| 3,036,624 A | 5/1962 | Carter |
| 3,190,466 A | 6/1965 | Hostetler |
| 4,596,107 A | 6/1986 | Pfleger, Sr. |
| 5,078,057 A | 1/1992 | Pearson |
| 5,297,668 A | 3/1994 | Zink |
| 5,699,891 A | 12/1997 | Gosdowski et al. |
| 5,765,675 A | 6/1998 | Draghetti et al. |
| 5,800,780 A | 9/1998 | Markin |
| 5,819,508 A | 10/1998 | Kraft et al. |
| 6,053,303 A | 4/2000 | Wang |
| 6,056,106 A | 5/2000 | Van Dyke, Jr. et al. |
| 6,520,313 B1 | 2/2003 | Kaarakainen et al. |
| 6,871,566 B2 | 3/2005 | Niwayama et al. |
| 7,152,504 B2 | 12/2006 | Itoh |
| 8,083,994 B2 | 12/2011 | Neeper et al. |
| 8,220,617 B2 | 7/2012 | Eberle |
| 8,877,128 B2 | 11/2014 | Fukugaki et al. |
| 8,973,736 B2 | 3/2015 | Johns et al. |
| 9,000,360 B2 | 4/2015 | DeWitte et al. |
| 9,063,103 B2 | 6/2015 | Pedrazzini |
| 9,164,113 B2 | 10/2015 | Friedman et al. |
| 9,248,982 B2 | 2/2016 | Eberhardt et al. |
| 9,267,957 B2 | 2/2016 | Haechler et al. |
| 9,321,621 B2 | 4/2016 | Kitano et al. |
| 9,481,528 B2 | 11/2016 | Pedrazzini |
| 9,527,233 B2 | 12/2016 | Winzinger |
| 9,733,161 B2 | 8/2017 | Nagai et al. |
| 9,910,054 B2 | 3/2018 | Johns |
| 2006/0245865 A1 | 11/2006 | Babson |
| 2007/0112399 A1 | 5/2007 | Baek |
| 2013/0233673 A1 | 9/2013 | Itoh |
| 2013/0239527 A1 | 9/2013 | Clarke et al. |
| 2014/0036276 A1 | 2/2014 | Gross et al. |
| 2014/0342465 A1 | 11/2014 | Haechler et al. |
| 2015/0177268 A1 | 6/2015 | Reisch et al. |
| 2015/0233955 A1 | 8/2015 | Nemoto et al. |
| 2017/0101272 A1 | 4/2017 | Cherubini et al. |
| 2017/0212139 A1 | 7/2017 | Jaeggi |
| 2017/0212141 A1 | 7/2017 | Schacher et al. |

FOREIGN PATENT DOCUMENTS

| | | |
|---|---|---|
| CN | 101309581 A | 11/2008 |
| CN | 102602697 A | 7/2012 |
| CN | 204613223 U | 9/2015 |
| EP | 2485058 A1 | 8/2012 |
| EP | 2253960 B1 | 5/2013 |
| EP | 2887071 A1 | 6/2015 |
| GB | 797685 | 7/1958 |
| JP | H07-234228 A | 9/1995 |
| JP | 2004-223646 A | 8/2004 |
| WO | 1983/000393 A1 | 2/1983 |
| WO | 2011/138448 A1 | 11/2011 |
| WO | 2014002953 A1 | 1/2014 |
| WO | 2014/147877 A1 | 9/2014 |
| WO | 2015/059620 A1 | 4/2015 |

LABORATORY SAMPLE CONTAINER CARRIER HANDLING APPARATUS AND LABORATORY SYSTEM

CROSS-REFERENCE TO RELATED APPLICATIONS

This application claims priority to EP 16152363.4, filed Jan. 22, 2016, which is hereby incorporated by reference.

BACKGROUND

The present disclosure relates to a laboratory sample container carrier handling apparatus and to a laboratory system.

There is a need for a laboratory sample container carrier handling apparatus and a laboratory system providing an efficient and reliable interface between a laboratory station and an operating device where the operating device delivers samples to be analyzed by the laboratory station

SUMMARY

According to the present disclosure, a laboratory sample container carrier handling apparatus is presented. The laboratory sample container carrier handling apparatus can comprise a first revolving device adapted to move sample container carriers along a first path, the first revolving device being placed at a first level, a second revolving device adapted to move sample container carriers along a second path, the second revolving device being placed at a second level being different from the first level, a first transport device adapted to transport sample container carriers to a first handover position associated with the first revolving device and/or adapted to transport sample container carriers away from the first handover position, a second transport device adapted to transport sample container carriers to a second handover position associated with the second revolving device and/or adapted to transport sample container carriers away from the second handover position, and a first lifting device adapted to lift a sample container carrier from a first lifting position associated with the first revolving device to a second lifting position associated with the second revolving device. An operating position can be associated with the first revolving device or the second revolving device. A sample container can be loaded in a sample container carrier placed at the operating position and/or a sample container can be unloaded from a sample container carrier placed at the operating position Accordingly, it is a feature of the embodiments of the present disclosure to provide for a laboratory sample container carrier handling apparatus and a laboratory system, providing an efficient and reliable interface between a laboratory station and an operating device, the operating device delivering samples to be analyzed by means of the laboratory station. Other features of the embodiments of the present disclosure will be apparent in light of the description of the disclosure embodied herein.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which.

DETAILED DESCRIPTION

Figure 1:
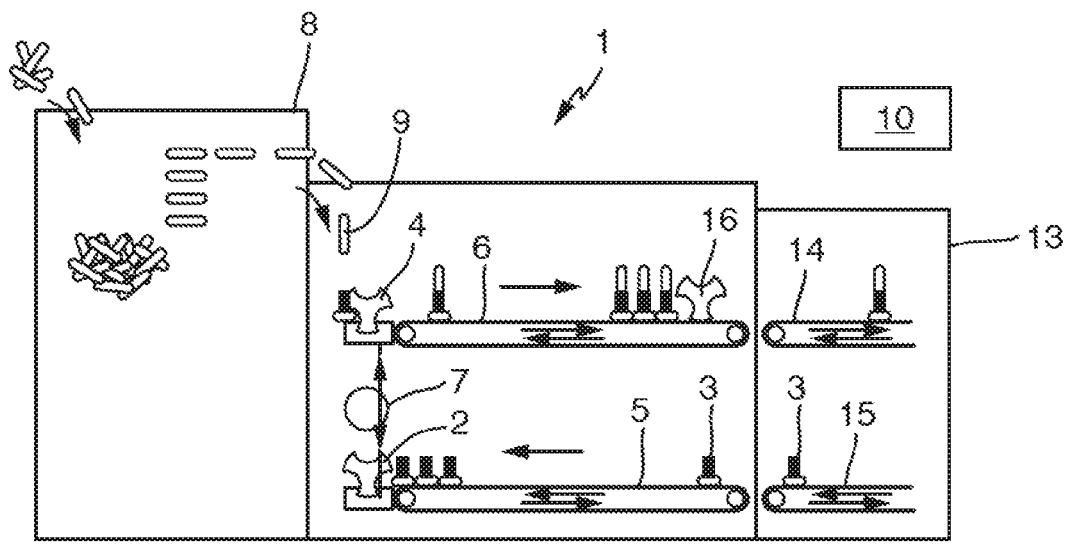
FIG. 1 illustrates schematically a laboratory system comprising an operating device, a laboratory sample container carrier handling apparatus, and a laboratory station according to an embodiment of the present disclosure.

In the following detailed description of the embodiments, reference is made to the accompanying drawings that form a part hereof, and in which are shown by way of illustration, and not by way of limitation, specific embodiments in which the disclosure may be practiced. It is to be understood that other embodiments may be utilized and that logical, mechanical and electrical changes may be made without departing from the spirit and scope of the present disclosure.

A laboratory sample container carrier handling apparatus, i.e. an apparatus for handling sample container carriers (and/or handling sample container carriers carrying sample containers and/or handling sample containers) used in diagnostic laboratories is presented. The container carriers may carry a single sample container or a plurality of sample containers.

The laboratory sample container carrier handling apparatus can comprise a first revolving device. The first revolving device can move, typically rotate, sample container carriers (carrying or not carrying a sample container) along a first path. The first revolving device can be placed at a first level such as, for example, a first horizontal level.

The laboratory sample container carrier handling apparatus can comprise a second revolving device. The second revolving device can move, typically rotate, sample container carriers (carrying or not carrying a sample container) along a second path being different from the first path. The second revolving device can be placed at a second level such as, for example a second horizontal level different from the first level.

The laboratory sample container carrier handling apparatus can comprise a first transport device. The first transport device can transport sample container carriers (carrying or not carrying a sample container) to a first handover position associated with, or assigned to, the first revolving device. Additionally or alternatively, the first transport device can transport sample container carriers (carrying or not carrying a sample container) away from the first handover position, e.g. to a laboratory station.

The laboratory sample container carrier handling apparatus can comprise a second transport device. The second transport device can transport sample container carriers (carrying or not carrying a sample container) to a second handover position associated with, or assigned to, the second revolving device and/or transports sample container carriers (carrying or not carrying a sample container) away from the second handover position, e.g. to the laboratory station.

The laboratory sample container carrier handling apparatus can comprise a first lifting device. The first lifting device, preferably vertically, can lift a sample container carrier (carrying or not carrying a sample container) from a first lifting position associated with, or assigned to, the first revolving device to a second lifting position associated with or assigned to the second revolving device. Typically, the first lifting position can have a different vertical level as the second lifting position.

An operating position can be associated with, or assigned to, the first revolving device or the second revolving device. An operating device, typically not part of the laboratory sample container carrier handling apparatus, can load a sample container in a sample container carrier placed at the operating position and/or the operating device can unload a sample container from a sample container carrier placed at the operating position.

The first path and/or the second path may form, typically vertically spaced, circular paths. The first circular path and the second circular path may have a common rotational axis. In other words, the first revolving device and the second revolving device may rotate around the same rotational axis. The rotational axis may be a vertical rotational axis. The radius of the first circular path and the radius of the second circular path may be identical.

The first revolving device and the second revolving device may be arranged substantially parallel and vertically spaced to each other, and the first path and the second path may be arranged coaxial to each other. The coaxial axis can be rectangular or angled with respect to the level of operation of the revolving devices.

The first transport device and/or the second transport device (or the transfer device of the second transport device) may be embodied as a conveyor belt.

The first revolving device may comprise three or more slots moving along the first path when the first revolving device is moving (typically rotating). Each slot may be adapted to receive and move (typically rotate) a corresponding sample container carrier. Accordingly, the second revolving device may comprise three or more slots moving (typically rotating) along the second path when the second revolving device is moving (typically rotating), each slot may be adapted to receive and move a corresponding sample container carrier. The slots of the first revolving device may be formed as slots in a first rotary disk. Accordingly, the slots of the second revolving device may be formed as slots in a second rotary disk. The slots may be distributed in a regular fashion over the corresponding rotary disk. The first revolving device and the second revolving device may have a star-shape.

In an operating state of the laboratory sample container carrier handling apparatus, one of the slots of the first revolving device may be assigned to the first handover position (or is in the first handover position), one of the slots of the first revolving device may be assigned to the first lifting position (or is in the first lifting position), and one or more of the slots of the first revolving device may be assigned to intermediate positions (or is/are in intermediate positions) located between the first handover position and the first lifting position, typically as seen in a direction of rotation of the first revolving device. Accordingly, in the predetermined operating state, one of the slots of the second revolving device may be assigned to the second handover position (or is in the second handover position), one of the slots of the second revolving device may be assigned to the second lifting position (or is in the second lifting position), and one of the slots of the second revolving device may be assigned to the operating position (or is in the operating position) located between the second handover position and the second lifting position. The intermediate positions may be placed between the handover position and the operating position, or the handover position and the lifting position, or the lifting position and the operating position, typically seen in a direction opposite to a direction of rotation of the second revolving device.

The second transport device may comprise a transfer device and a second lifting device adapted to vertically lift a sample container carrier from a third lifting position associated with or assigned to the second revolving device to the transfer device. The transfer device may be adapted to provide sample container carriers at a third level different from the first and second level.

The operating position may be placed or located on the second path.

The second revolving device may move (typically rotate) sample container carriers to and from the operating position.

A rotating direction of the first revolving device may be opposite to a rotating direction of the second revolving device.

The first and/or second lifting device may comprise a platform for carrying the respective sample container carrier. The platform can comprise a region having an increasing horizontal width (size) towards a center of a respective revolving device.

A laboratory system can comprise a laboratory sample container carrier handling apparatus as described above.

The laboratory system can further comprise an operating device. The operating device can load a sample container in a sample container carrier placed at the operating position and/or can unload a sample container from a sample container carrier placed at the operating position.

The laboratory system can further comprise a laboratory station adapted to process sample containers, and/or samples contained in the sample containers.

A laboratory station may be a pre-analytical, an analytical or a post-analytical station.

Pre-analytical stations may be adapted to perform any kind of pre-processing of samples, sample containers and/or sample container carriers.

Analytical stations may be adapted to use a sample or part of the sample and a reagent to generate a measuring signal. The measuring signal can indicate if and in which concentration, if any, an analyte exists.

Post-analytical stations may be adapted to perform any kind of post-processing of samples, sample containers and/or sample container carriers.

The pre-analytical, analytical and/or post-analytical stations may comprise at least one of a decapping station, a recapping station, a centrifugation station, an archiving station, a pipetting station, a sorting station, a tube type identification station, and a sample quality determining station.

The laboratory station can be operatively coupled to the first transport device and to the second transport device. For example, the laboratory station may provide sample container carriers not carrying sample containers (denoted as empty sample container carriers) to the first transport device. The second transport device may provide sample container carriers carrying sample containers (denoted as loaded sample container carriers) to the laboratory station. The laboratory station can process the samples contained in the sample containers.

The laboratory system may comprise a control device, e.g. in the form of a microprocessor or a personal computer. The control device can control the operating device such that the operating device can load a sample container in a sample container carrier placed at the operating position and/or such that the operating device can unload a sample container from a sample container carrier placed at the operating position.

The control device may control the first lifting device such that the first lifting device can lift a sample container carrier from the first lifting position to the second lifting position simultaneously to the loading/unloading of the sample container.

The control device may control the laboratory station to provide an empty sample container carrier to the first transport device, successively control the first transport device to provide the empty sample container carrier to the first handover position of the first revolving device, successively control the first revolving device to move or rotate the empty sample container carrier to the first lifting position, successively control the first lifting device to lift the empty sample container carrier from the first lifting position to the second lifting position, successively control the second revolving device to move or rotate the empty sample container carrier to the operating position, successively control the operating device to load a sample container in the empty sample container carrier, successively control the second revolving device to move or rotate the loaded sample container carrier to the second handover position, and successively control the second transport device to transport the loaded sample container carrier from the second handover position to the laboratory station. The laboratory station may then perform an analysis of the sample contained in the sample container provided to the laboratory station.

Self-evidently, the first revolving device, the second revolving device, the first transport device, the second transport device, the lifting device, the operating device may respectively comprise drives, e.g. electric motors, to cause a desired movement of the respective devices.

Referring initially to FIG. 1, FIG. 1 schematically shows a laboratory system comprising an operating device 8, a laboratory sample container carrier handling apparatus 1, and a laboratory station 13.

The operating device 8 can comprise sample container storage. A user can fill the sample container storage with closed sample containers 9 in a bulk commodity. The sample containers 9 can comprise medical samples, e.g. biological liquid samples such as blood samples. The operating device 8 can remove single sample containers 9 from the container storage and provide the single sample containers 9 to the sample container carrier handling apparatus 1, as will be described in more detail below.

A laboratory station 13 can process samples contained in the sample containers 9. The laboratory station 13 can operatively be coupled to the sample container carrier handling apparatus 1, as will be described in more detail below.

The laboratory station 13 can comprise a first conveyor belt 15 placed at a first vertical level. By use of the first conveyor belt 15, the laboratory station 13 can provide empty sample container carriers 3 to a first transport device of the laboratory sample container carrier handling apparatus 1. The first transport device can be a conveyor belt 5. A transfer operation can e.g. be triggered by the laboratory sample container carrier handling apparatus 1.

The laboratory station 13 can comprise a second conveyor belt 14 placed at a second vertical level. The second vertical level can differ from the first vertical level. By use of the second conveyor belt 14, the laboratory station 13 can receive sample container carriers 3 carrying a sample container 9.

The first and second conveyor belts 15 and 14 can form an interface to the laboratory sample container carrier handling apparatus 1.

The laboratory sample container carrier handling apparatus 1 can serve as a connector between the operating device 8 and the laboratory station 13. The laboratory sample container carrier handling apparatus 1 can receive empty sample container carriers 3 from the first conveyor belt 15 of the laboratory station 13, transport the empty sample container carriers 3 to an operating position OP (see FIG. 2) within the laboratory sample container carrier handling apparatus 1. Sample containers 9 can be loaded in the empty sample container carriers 3 placed at the operating position OP. The laboratory sample container carrier handling apparatus 1 can provide the loaded sample container carriers 3 to the second conveyor belt 14 of the laboratory station 13.

Figure 2:
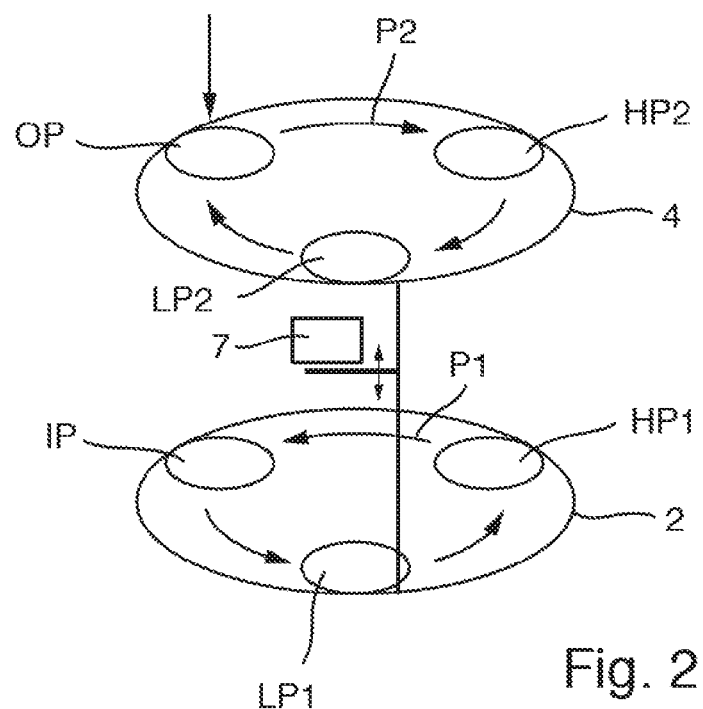
FIG. 2 illustrates schematically paths formed by revolving devices, wherein the revolving devices are part of the laboratory sample container carrier handling apparatus shown in FIG. 1 according to an embodiment of the present disclosure.
Figure 3:
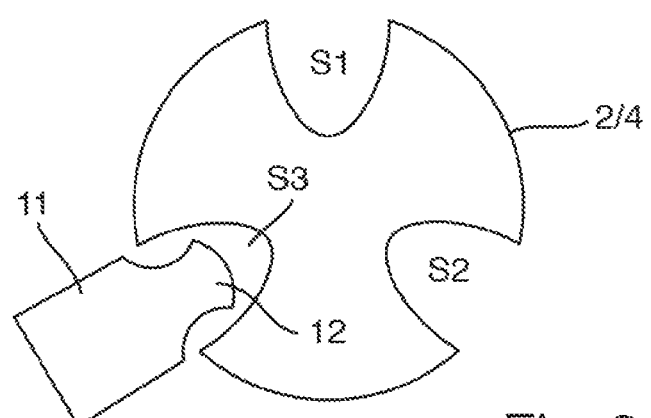
FIG. 3 illustrates schematically a lifting device, wherein the lifting device is part of the laboratory sample container carrier handling apparatus shown in FIG. 1 according to an embodiment of the present disclosure.

Referring to FIGS. 2 and 3, the laboratory sample container carrier handling apparatus 1 can comprise a first revolving device 2 adapted to move sample container carriers 3 along a first circular path P1. The first revolving device 2 can be placed at the first level. The laboratory sample container carrier handling apparatus 1 can further comprise a second revolving device 4 adapted to move sample container carriers 3 along a second circular path P2. The second revolving device 4 can be placed at the second level.

The first circular path P1 and the second circular path P2 can have a common rotational axis substantially perpendicular to a transport direction of the transport devices 5 and 6.

The first transport device 5 can transport empty sample container carriers 3 to a first handover position HP1 associated with the first revolving device 2.

The second transport device 6 can transport sample container carriers 3 from a second handover position HP2 associated with the second revolving device 4 to the laboratory station 13.

The laboratory sample container carrier handling apparatus 1 can comprise a lifting device 7. The lifting device 7 can lift a sample container carrier 3 from a first lifting position LP1 associated with the first revolving device 2 to a second lifting position LP2 associated with the second revolving device 4.

The operating position OP can be associated with the second revolving device 4. Sample containers 9 can be loaded in sample container carriers 3 placed at the operating position OP.

Referring to FIG. 3, the first and the second revolving device 2/4 respectively can comprise three slots S1, S2, S3 formed in a rotary disk. Each slot S1, S2, S3 can be adapted to receive and rotate a sample container carrier 3 along the circular path P1 and P2, respectively.

In a predetermined operating state or angularity of the first revolving device 2, one of the slots can be assigned to the first handover position HP1, one of the slots can be assigned to the first lifting position LP1, and of the slots can be assigned to an intermediate position IP located between the first handover position HP1 and the first lifting position LP1.

In a predetermined operating state or angularity of the of the second revolving device 4, one of the slots can be assigned to the second handover position HP2, one of the slots can be assigned to the second lifting position LP2, and one of the slots can be assigned to the operating position OP located between the second handover position HP2 and the second lifting position LP2.

The first revolving device 2 can rotate opposite to the second revolving device 4.

Referring to FIG. 3, the lifting device 7 can comprise a platform 11 for carrying/lifting a sample container carrier 3. The platform 11 can comprise a region 12 having an increasing horizontal width towards a center of a respective revolving device 2, 4. This embodiment can increase the base area of the sample container carriers 3 in the relevant regions and at the same time increase the free space between the revolving device 2/4 and the platform 11, thus avoiding collisions between the revolving device 2/4 and the platform 11.

The laboratory system can further comprise a control device 10. The control device 10 can control the operating device 8 such that the operating device 8 can load a sample container 9 in a sample container carrier 3 placed at the operating position OP, and at the same time, can control the lifting device 7 such that the lifting device 7 can simultaneously lift a sample container 3 from the first lifting position LP1 to the second lifting position LP2. By performing these steps simultaneously, sample throughput can be optimized.

The control device 10 may implement a transfer cycle as follows. The control device 10 can control the laboratory station 13 to provide an empty sample container carrier 3 to the first transport device 5. Then, the control device 10 can control the first transport device 5 to transport the empty sample container carrier 3 to the first handover position HP1 of the first revolving device 2. Then, the control device 10 can control the first revolving device 2 to rotate the empty sample container carrier 3 to the intermediate position IP. When the empty sample container carrier 3 is positioned at the intermediate position IP, another sample container carrier 3 may be lifted from the first lifting position LP1 to the second lifting LP2. Then, the control device 10 can control the first revolving device 2 to rotate the empty sample container carrier 3 to the first lifting position LP1. Then, the control device 10 can control the lifting device 7 to lift the empty sample container carrier 3 from the first lifting position LP1 to the second lifting position LP2. The platform 11 of the lifting device 7 can move through the corresponding slots of the revolving devices 2/4. Then, the control device 10 can control the second revolving device 2 to rotate the empty sample container carrier 3 to the operating position OP. Then, the control device 10 can control the operating device 8 to load a sample container 9 in the empty sample container carrier 3. The operating device 8 may comprise suitable methods for loading a sample container 9 in the empty sample container carrier 3, e.g. a pick-and-place and the like. Then, the control device 10 can control the second revolving device 2 to rotate the loaded sample container carrier 3 to the second handover position HP2. Finally, the control device 10 can control the second transport device 6 to transport the loaded sample container carrier 3 from the second handover position HP2 to the laboratory station 13.

The above cycle has been described with respect to a single and exemplary sample container carrier 3 travelling from a start position to a destination position. Self-evidently, multiple sample container carriers 3 can travel through the laboratory sample container carrier handling apparatus 1 simultaneously in a pipelined fashion. In other words, the above described steps may overlap in time with respect to different sample container carriers 3. If e.g. a plurality of sample container carriers 3 is transported by the conveyor belt 5, at least some of the sample container carriers 3 may jam before the first revolving device 2. Typically, the conveyor belt 5 can run continuously. Thus, the foremost sample container carrier 3 can automatically be inserted into the corresponding slot of the first revolving device 2, when the first revolving device 2 rotates. Accordingly, a sample container carrier 3 being rotated into the second handover position HP2 can be automatically removed from the second revolving device 4 by the conveyor belt 6.

The revolving devices 2/4 can rotate synchronized with each other, in opposite directions in approximately 120 angular degree steps. The angular degree steps can be calculated as 360°/(number of slots).

In the depicted embodiments, the revolving devices 2/4 can each comprise 3 slots. Self-evidently, the revolving devices 2/4 may comprise more than 3 slots, e.g. 5, 7, or 9 slots, so that the revolving devices can provide more than one operating position OP or can even be used as a buffer for sample containers 9 or empty sample container carriers 3.

The laboratory sample container carrier handling apparatus may comprise an optional sample container carrier individualizer 16 adapted to provide sample container carriers 3 one by one to the conveyor belt 14.

It is noted that terms like "preferably," "commonly," and "typically" are not utilized herein to limit the scope of the claimed embodiments or to imply that certain features are critical, essential, or even important to the structure or function of the claimed embodiments. Rather, these terms are merely intended to highlight alternative or additional features that may or may not be utilized in a particular embodiment of the present disclosure.

For the purposes of describing and defining the present disclosure, it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the present disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure.

We claim:

1. A laboratory sample container carrier handling apparatus, the laboratory sample container carrier handling apparatus comprising:
    a first revolving device adapted to move sample container carriers along a first path, the first revolving device being placed at a first level;
    a second revolving device adapted to move sample container carriers along a second path, the second revolving device being placed at a second level being different from the first level;
    a first transport device adapted to transport sample container carriers to a first handover position associated with the first revolving device or transport sample container carriers away from a first handover position;
    a second transport device adapted to transport sample container carriers to a second handover position associated with the second revolving device or transport sample container carriers away from a second handover position; and
    a first lifting device adapted to lift a sample container carrier from a first lifting position associated with the first revolving device to a second lifting position associated with the second revolving device, wherein an operating position is associated with the second revolving device and wherein a sample container is loaded in a sample container carrier placed at the operating position or a sample container is unloaded from a sample container carrier placed at the operating position.

2. The laboratory sample container carrier handling apparatus according to claim 1, wherein the first path and/or the second path are circular paths.

3. The laboratory sample container carrier handling apparatus according to claim 2, wherein the first circular path and the second circular path have a common rotational axis.

4. The laboratory sample container carrier handling apparatus according to claim 1, wherein the first revolving device has three slots moving along the first path when the first revolving device is moving, wherein each slot is adapted to receive and move a sample container carrier, and/or the second revolving device has three slots moving along the second path when the second revolving device is moving, wherein each slot is adapted to receive and move a sample container carrier.

5. The laboratory sample container carrier handling apparatus according to claim 4, wherein, in a predetermined operating state, one of the slots of the first revolving device is assigned to the first handover position, one of the slots of the first revolving device is assigned to the first lifting position, and one or more of the slots of the first revolving device are assigned to intermediate positions located between the first handover position and the first lifting position.

6. The laboratory sample container carrier handling apparatus according to claim 4, wherein, in a predetermined operating state, one of the slots of the second revolving device is assigned to the second handover position, one of the slots of the second revolving device is assigned to the second lifting position, and one of the slots of the second revolving device is assigned to the operating position located between the second handover position and the second lifting position.

7. The laboratory sample container carrier handling apparatus according to claim 1, wherein the operating position is placed on the second path.

8. The laboratory sample container carrier handling apparatus according to claim 7, wherein the second revolving device is adapted to move sample container carriers to and from the operating position.

9. The laboratory sample container carrier handling apparatus according to claim 1, wherein the first revolving device rotates opposite to the second revolving device.

10. The laboratory sample container carrier handling apparatus according to claim 1, wherein the first lifting device has a platform for carrying the respective sample container carrier and wherein the platform has a region having an increasing horizontal width towards a center of a respective revolving device.

11. The laboratory sample container carrier handling apparatus according to claim 1, wherein the first transport device and/or the second transport device is/are embodied as a conveyor belt.

12. A laboratory system, the laboratory system comprising:
    a laboratory sample container carrier handling apparatus according to claim 1;
    an operating device adapted to load a sample container in a sample container carrier placed at the operating position and/or adapted to unload a sample container from a sample container carrier placed at the operating position; and
    a laboratory station adapted to process sample containers and/or samples contained in the sample containers, wherein the laboratory station is operatively coupled to the first transport device and to the second transport device.

13. The laboratory system according to claim 12, further comprising,
    a control device, wherein the control device is configured to control the operating device such that the operating device loads a sample container in a sample container carrier placed at the operating position and/or such that the operating device unloads a sample container from a sample container carrier placed at the operating position, and wherein the control device is configured to control the first lifting device such that the first lifting device simultaneously lifts a sample container carrier from the first lifting position to the second lifting position.

14. The laboratory system according to claim 13, wherein the control device is adapted:
    to control the laboratory station to provide an empty sample container carrier to the first transport device,
    to control the first transport device to provide the empty sample container carrier to the first handover position of the first revolving device,
    to control the first revolving device to move the empty sample container carrier to the first lifting position,
    to control the first lifting device to lift the empty sample container carrier from the first lifting position to the second lifting position,
    to control the second revolving device to move the empty sample container carrier to the operating position,
    to control the operating device to load a sample container in the empty sample container carrier,
    to control the second revolving device to move the loaded sample container carrier to the second handover position, and
    to control the second transport device to transport the loaded sample container carrier from the second handover position to the laboratory station.

* * * * *